(12) United States Patent
Ryan

(10) Patent No.: US 7,163,542 B2
(45) Date of Patent: Jan. 16, 2007

(54) ADJUSTABLE DEPTH DRILL BIT

(75) Inventor: Christopher J. Ryan, West Chester, PA (US)

(73) Assignee: Synthes (U.S.A.), Paoli, PA (US)

( * ) Notice: Subject to any disclaimer, the term of this patent is extended or adjusted under 35 U.S.C. 154(b) by 227 days.

(21) Appl. No.: 10/814,696

(22) Filed: Mar. 30, 2004

(65) Prior Publication Data
US 2005/0222571 A1 Oct. 6, 2005

(51) Int. Cl.
A61B 17/17 (2006.01)

(52) U.S. Cl. .................................................. 606/96

(58) Field of Classification Search ............ 606/79, 606/80, 86, 96, 99, 104
See application file for complete search history.

(56) References Cited

U.S. PATENT DOCUMENTS

| | | | |
|---|---|---|---|
| 412,952 A | 10/1889 | Elterich | |
| 2,344,143 A | 3/1944 | Harding | |
| 3,301,101 A | 1/1967 | McEwen | |
| 3,576,076 A | 4/1971 | Weissman | |
| 3,855,705 A | 12/1974 | Malmin | |
| 4,039,266 A | 8/1977 | O'Connell | |
| 4,142,517 A | 3/1979 | Stavropoulos et al. | |
| 4,341,206 A | 7/1982 | Perrett et al. | |
| 4,521,144 A | 6/1985 | Ginter | |
| 4,521,145 A | 6/1985 | Bieler | |
| 4,549,538 A | 10/1985 | Schadrack, III et al. | |
| 4,552,370 A | 11/1985 | Baumgartner | |
| 4,637,539 A | 1/1987 | Turcott et al. | |
| 4,693,656 A | 9/1987 | Guthrie | |
| 4,710,075 A | 12/1987 | Davison | |
| 4,877,359 A | 10/1989 | Kolacek | |
| 4,978,261 A | 12/1990 | Wright, III | |
| 4,998,881 A | 3/1991 | Lauks | |
| 5,051,043 A | 9/1991 | Spitznagel | |
| 5,051,092 A | 9/1991 | Miller | |
| 5,078,552 A | 1/1992 | Albel | |
| 5,180,388 A | 1/1993 | DiCarlo | |
| 5,190,548 A | 3/1993 | Davis | |
| 5,382,120 A | 1/1995 | Parsons | |
| 5,382,250 A | 1/1995 | Kraus | |
| 5,409,490 A | 4/1995 | Ethridge | |

(Continued)

FOREIGN PATENT DOCUMENTS

DE 38 00 482 7/1989

OTHER PUBLICATIONS

International Search Report for PCT Application Ser. No. PCT/US03/36619.

(Continued)

Primary Examiner—Eduardo C. Robert
Assistant Examiner—Richard Shaffer
(74) Attorney, Agent, or Firm—Jones Day

(57) ABSTRACT

A drill guide with integral drill bit is provided for drilling a hole into bone. The drill guide may have a housing for engaging a screw hole of a bone plate to fix the trajectory of the drill guide and drill with respect to the bone plate. An adjustable stop assembly is also provided and is axially slidable along the drill bit. The adjustable stop has a drill bit engaging mechanism to selectively lock the adjustable stop to the drill bit at a desired location to limit the depth that the drill may penetrate into the bone.

53 Claims, 11 Drawing Sheets

U.S. PATENT DOCUMENTS

| | | |
|---|---|---|
| 5,423,824 A | 6/1995 | Akerfeldt et al. |
| 5,520,692 A | 5/1996 | Ferrante |
| 5,591,207 A | 1/1997 | Coleman |
| 5,634,927 A | 6/1997 | Houston et al. |
| 5,741,267 A | 4/1998 | Jorneus et al. |
| 5,782,835 A | 7/1998 | Hart et al. |
| 5,785,522 A | 7/1998 | Bergström et al. |
| 5,795,110 A | 8/1998 | Wirth, Jr. et al. |
| 5,810,826 A | 9/1998 | Åkerfeldt et al. |
| 5,810,828 A | 9/1998 | Lightman et al. |
| 5,890,897 A | 4/1999 | Kruger et al. |
| 5,895,389 A | 4/1999 | Schenk et al. |
| 5,941,706 A | 8/1999 | Ura |
| 5,993,453 A * | 11/1999 | Bullara et al. ............... 606/79 |
| 6,015,411 A | 1/2000 | Ohkoshi et al. |
| 6,017,348 A | 1/2000 | Hart et al. |
| 6,110,178 A | 8/2000 | Zech et al. |
| 6,120,506 A | 9/2000 | Kohrs et al. |
| 6,193,721 B1 * | 2/2001 | Michelson ................... 606/70 |
| 6,235,035 B1 | 5/2001 | Boukhris |
| 6,283,966 B1 | 9/2001 | Houfburg |
| 6,287,313 B1 | 9/2001 | Sasso |
| 6,306,142 B1 | 10/2001 | Johanson et al. |
| 6,524,318 B1 * | 2/2003 | Longhini et al. ............. 606/86 |
| 6,592,586 B1 | 7/2003 | Michelson |
| 6,951,562 B1 * | 10/2005 | Zwirnmann ................... 606/80 |
| 2001/0012942 A1 * | 8/2001 | Estes et al. ................. 606/105 |

OTHER PUBLICATIONS

W. Lorenz Surgical, Selected Articles & Instrumentation, No Date.

Stryker Leibinger, Delta System Resorbable Implant Technology, No Date.

* cited by examiner

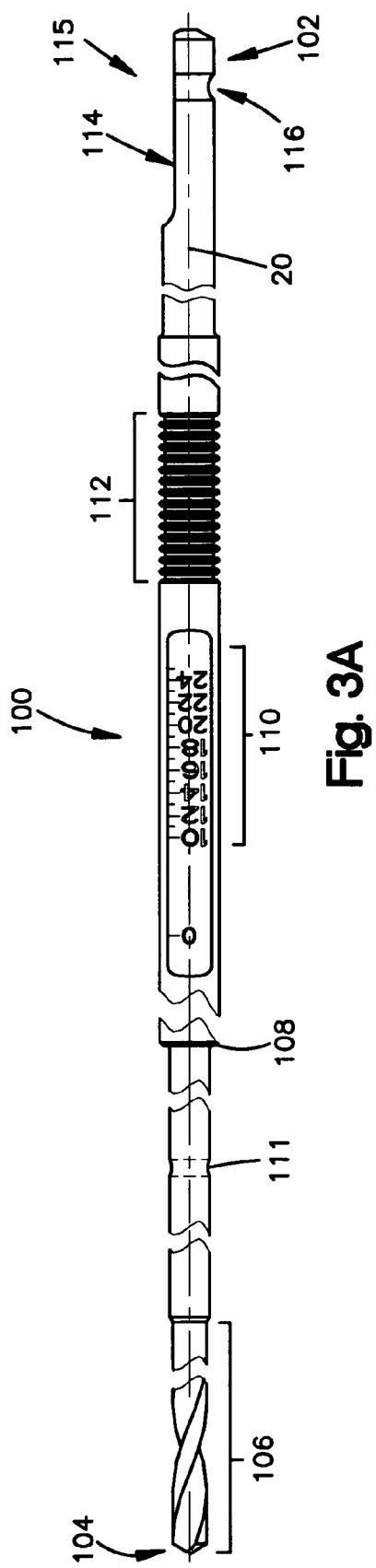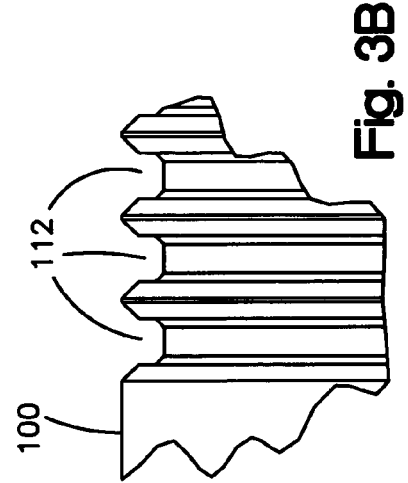
Fig. 3A
Fig. 3B

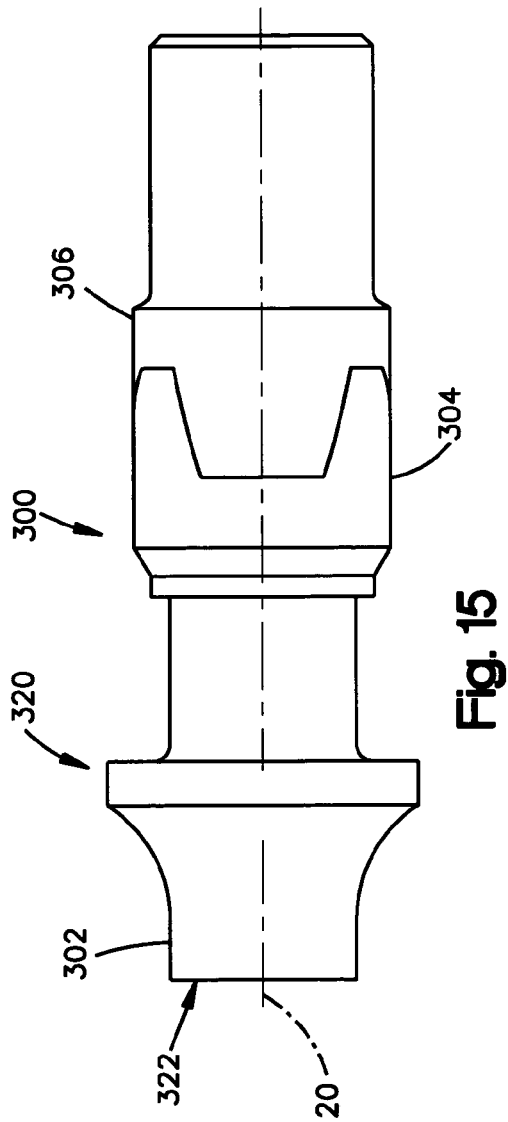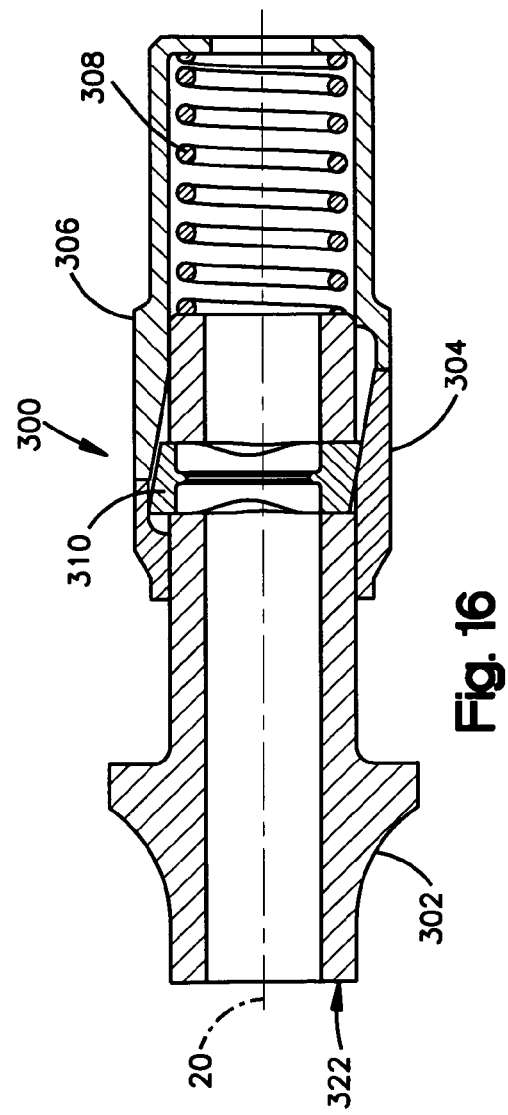

ADJUSTABLE DEPTH DRILL BIT

FIELD OF THE INVENTION

The present invention relates to a device for boring a hole into a bone. More particularly, the device is removably attachable to a bone screw hole of a fixation plate and provides a depth limiting function for precision boring of the bone in precise alignment with the bone screw hole of the bone fixation plate.

BACKGROUND

The use of surgical fixation plates for a variety of orthopaedic applications is a widely accepted. Fixation plates are used by surgeons to stabilize, mend, or align fractured or diseased bones as well as to apply compression or tension to bones and to fuse joints between two or more bones. Typically, fixation plates are fastened to the bone with at least one, and often a plurality, of fasteners such as bone screws that are installed through bone screw holes in the plate. Proper orientation and alignment of the fasteners with the bone plate and secure fixation of the bone plate to the bone can mitigate potential complications after implantation.

Fixation plates used in spinal applications must be installed with special care. The margin for error in spinal surgery is small, particularly because of the sensitivity of the spinal cord and the risk inherent in performing invasive procedures near the spinal cord. Furthermore, the dimensions of vertebral bone available for receiving fasteners are fairly constrained.

Screws used to secure the bone plate often must be precisely aligned to facilitate retention of the fasteners in the bone. In some instances the fasteners may be particularly aligned in order facilitate compression between opposing bone segments. Misalignment of the screw within the screw hole of the plate may increase the risk of tissue damage, bone screw failure, fixation failure, and/or bone screw 'back-out' thus increasing the risk of further injury to the patient and defeating the usefulness of the plate. Locking plates in particular demand the aforementioned precise fastener alignment for proper function.

Drill guides are often used to facilitate the alignment of bone screw pilot holes and the insertion of bone screws. A typical drill guide attaches or abuts against an associated fixation plate and includes a guide tube for guiding surgical tools (e.g. awls, taps, drills, screws and screwdrivers) toward and through the bone screw hole in the plate. One drawback of the typical drill guide is that it is yet another piece of surgical equipment that must be separately manipulated and accounted for at the surgical suite. A surgeon must manipulate both the tool that is inserted through the drill guide and the drill guide itself, or must have assistance in doing so. This often complicates the surgical procedure, increases the chance for error, and increases the length of surgical procedure.

Traditional drill guides have included depth limiting arrangements of different sorts for limiting the penetration depth of drills, awls, taps, and other similar bone piercing and boring tools. Currently, there are generally two methods of limiting drilling depth. One consists of an adjustable drill guide that is typically a tubular member with a handle, where the tubular member receives drilling tools therethrough. The tube typically has a stop mechanism that engages with the drilling tool, such as opposing surfaces on the drill guide and on the drill bit that come in contact. Often, one of the components surfaces is adjustable by a threaded mechanism or the like, such that the penetration depth of the component can be adjusted. Another traditional mechanism is a tubular drill guide having a single stop that interacts with different drill bits, where each drill bit has a stop at a different location according to a preferred drilling depth.

Providing a surgeon with the ability to select a preferred drilling depth increases the efficiency and accuracy of many surgical procedures. This is because many different lengths of screw are used for different procedures and different patient anatomy's. Furthermore, the depth of a bone screw hole, and the length of a bone screw also depends on the bone quality into which the screw is to penetrate. Yet another consideration is the amount of injury that may result if the drilling procedure and or bone screw penetrate beyond a particular depth. For example, the injury that may result from a misplaced, mis-angled, or misjudged penetration depth of a bone screw placed into a vertebra often can be drastic and permanent.

Accordingly, a device and method for combining the beneficial functions of a drill guide and a depth limiting guide into a single surgical tool would be highly desirable.

SUMMARY OF THE INVENTION

According to one embodiment, there is provided a tool comprising a drill bit having a proximal end and a distal end, the distal end configured to cut bone. A housing may also be provided having proximal and distal ends and a bore configured to slidably receive the drill bit. The second end of the housing may be associated with a bone portion into which the drill bit will be extended. An adjustable depth stop assembly may be provided having proximal and distal ends and a bore configured to slidably receive the drill bit, the depth stop further having a portion configured to selectively lock the drill bit to the bore. Thus, when the drill bit is locked to the adjustable depth stop the proximal end of the housing is located a first axial distance from the distal end of the adjustable depth stop so that the first axial distance is proportional to a maximum drilling depth into the bone portion.

The distal end of the housing may be configured to engage the bone portion directly, or the distal end of the housing may configured to engage a bone fixation element such as a bone plate or a pedicle screw clamping element. The pedicle screw clamping element may be any such element known in the art used to connect a pedicle screw to a spine fixation rod or plate to bridge adjacent vertebra so as to fix their relative positions during, for example, spinal fusion procedures.

Where the bone fixation element comprises a bone plate the distal end of the housing may be configured to engage a fastener hole of the plate. The distal end of the housing may further comprising threads configured to engage corresponding threads of the fastener hole. The distal end of the housing may further be configured to engage a screw hole of a bone plate to fix the trajectory of the drill bit with respect to the bone plate and the bone portion. The drill bit may be axially positionable with respect to the housing and the drill bit may also having an extended position in which the distal end of the drill bit extends distally beyond the housing distal end. The drill bit may also have a retracted position in which the distal end of the drill bit does not extend distally beyond the housing distal end.

The tool housing may comprise a spring having a first surface associated with the housing and a second surface associated with the drill bit, where the spring is operable to bias the drill in the retracted position. The drill bit may have an axial engagement portion configured to engage a corresponding axial engagement portion of the housing to prevent the distal end of the drill bit from moving axially past the proximal end of the housing. The axial engagement portions of the drill bit and housing may comprise a pin and a shoulder, respectively. The housing may further comprise proximal and distal housing portions. The proximal housing portion may have a spring operable to bias the drill in the retracted position, while the distal housing portion may have threads for engaging a bone screw hole of the bone plate. The proximal end of the distal housing further may have protrusion and recess elements configured to engage a respective recess and protrusion elements on the distal end of the proximal housing to rotationally fix the two housing portions. The housing further may have a retainer for removably coupling the proximal and distal housing portions so that the housing portions may be disassembled to facilitate cleaning and/or sterilization of the tool.

The proximal housing portion of the tool may further have a proximal end having an increased diameter to allow gripping by a user. The proximal housing portion further may have a proximal stop surface configured to engage the adjustable depth stop assembly.

The adjustable depth stop may have an adjustment sleeve configured to slidably engage the drill bit, and a shuttle member adapted to be slidable with respect to the adjustment sleeve between a first position in which the adjustable depth stop is axially locked to the drill bit and a second position in which the adjustable depth stop is axially movable with respect to the drill bit. Moving the shuttle between first and second positions may comprise moving the shuttle along an axis substantially perpendicular to the longitudinal axis of the drill bit. Moving the shuttle between first and second positions may also comprise moving the shuttle along an axis substantially non-parallel to the longitudinal axis of the drill bit. The shuttle may further comprise a drill bit engaging surface, the drill bit further comprising a shuttle engaging surface, and one of the drill bit engaging surface and shuttle engaging surface may comprise a projection and the other comprises a recess.

The adjustable depth stop may further comprise a locking sleeve associated with the adjustment sleeve, where the locking sleeve is co-operable with the shuttle to move the shuttle between the first and second positions. The locking sleeve and shuttle further may have corresponding tapered sliding surfaces each of which forms an oblique angle with respect to the longitudinal axis of the drill bit, wherein axial movement of the locking sleeve moves the shuttle between the first and second positions. The shuttle may be axially fixed to the adjustment sleeve, and the locking sleeve may be axially translatable along the adjustment sleeve. Thus, moving the locking sleeve along the adjustment sleeve in a first direction may cause the shuttle to move toward the first position. Moving the locking sleeve along the adjustment sleeve in a second direction may cause the shuttle to move toward the second position.

The adjustable depth stop may further comprise a spring associated with the adjustment sleeve to bias the shuttle in the first position. The adjustment sleeve may also have a distal stop surface configured to engage the housing.

In an alternative embodiment, a tool may be provided comprising a drill bit having proximal and distal ends and a longitudinal axis. The proximal end of the drill bit may be configured to connect to a driving attachment and the distal end may have a cutting surface for cutting a hole in a bone. The drill bit may also having an extended position corresponding to a first drilling depth into the bone. A housing may further be provided having proximal and distal ends and a longitudinal bore. The drill bit may be axially positionable within the bore, and the proximal end of the housing may further having a stop surface. The distal end of the housing may be associated with a bone portion. An adjustable depth stop assembly may be provided having proximal and distal ends and a longitudinal bore. The drill bit may be selectively axially lockable within the bore, and the distal end may comprise a stop surface configured to engage the housing stop surface. The assembly may further having unlocked and locked configurations so that the drill bit is axially translatable within the assembly when the assembly is in the unlocked position and the drill bit is axially fixed with respect to the assembly when the assembly is in the locked configuration. Thus, adjusting the distance between the respective stop surfaces of the housing and the depth stop assembly may adjust the first drilling depth into the bone portion.

The distal end of the housing may further be configured to engage a fastener hole of a bone plate, and the distal end may also have threads configured to engage corresponding threads of the hole in the plate. The distal end of the housing also may be configured to engage the fastener hole of the bone plate in order to fix the trajectory of the drill bit with respect to the bone plate.

The drill bit further may have a retracted position in which the distal end of the drill bit does not extend distally beyond the housing distal end. The housing may further have a spring having a first surface associated with the housing and a second surface associated with the drill bit, the spring operable to bias the drill in the retracted position.

The drill bit further may have an axial engagement portion configured to engage a corresponding axial engagement portion of the housing to prevent the distal end of the drill bit from moving axially past the proximal end of the housing. The axial engagement portions of the drill bit and housing may comprise a pin and a shoulder, respectively.

The housing further may comprise proximal and distal housing portions, and the proximal housing may comprise a spring operable to bias the drill in the retracted position. The distal housing may comprise threads for engaging a bone screw hole of the bone plate. The proximal end of the distal housing further may comprise protrusion and recess elements configured to engage respective recess and protrusion elements on the distal end of the proximal housing to rotationally fix the two housings. The housing further may comprise a retainer for removably coupling the proximal and distal housings, such that the proximal and distal housings can be decoupled to facilitate cleaning and/or sterilization of the tool.

The proximal housing further comprising a proximal end having an increased diameter to allow gripping by a user. The proximal housing portion may also have a proximal stop surface configured to engage the adjustable depth stop assembly. The adjustable depth stop further may comprise an adjustment sleeve configured to slidably engage the drill bit, and may also have a shuttle member adapted to be slidable with respect to the adjustment sleeve between a first position in which the adjustable depth stop is axially locked to the drill bit and a second position in which the adjustable depth stop is axially movable with respect to the drill bit. Thus, moving the shuttle between first and second positions comprises moving the shuttle along an axis substantially perpendicular to the longitudinal axis of the drill bit. Furthermore, moving the shuttle between first and second positions may comprise moving the shuttle along an axis substantially non-parallel to the longitudinal axis of the drill bit.

The shuttle further may comprise a drill bit engaging surface, and the drill bit may further comprise a shuttle engaging surface. One of the drill bit engaging surface and shuttle engaging surface may be a projection and the other may be a recess.

The adjustable depth stop further may comprise a locking sleeve associated with the adjustment sleeve, and the locking sleeve may be co-operable with the shuttle to move the shuttle between the first and second positions. The locking sleeve and shuttle further may comprise corresponding tapered sliding surfaces each of which forms an oblique angle with respect to the longitudinal axis of the drill bit such that axial movement of the locking sleeve may move the shuttle between the first and second positions.

The shuttle also may be axially fixed to the adjustment sleeve, and the locking sleeve may be axially translatable along the adjustment sleeve, such that moving the locking sleeve along the adjustment sleeve in a first direction may cause the shuttle to move toward the first position. Furthermore, moving the locking sleeve along the adjustment sleeve in a second direction may cause the shuttle to move toward the second position. The adjustable depth stop further may comprise a spring associated with the adjustment sleeve to bias the shuttle in the first position.

A method of drilling a hole to a desired depth is also disclosed. The method may comprise the steps of (a) providing a drill bit having a housing and an adjustable depth stop assembly, where the drill bit is slidably receivable within a bore in the housing, the drill bit further being receivable in, and adjustably lockable with respect to, a bore in the depth stop assembly; (b) associating the housing with a bone segment; (c) adjusting the axial position of the depth stop assembly along the drill bit to position the housing a first distance from the depth stop assembly; and (d) drilling a hole into the bone with the drill bit such that the hole in the bone has a depth proportional to the first distance.

The step of associating the housing with a bone segment may further comprise engaging the housing with a fastener hole of a bone plate. The method may also comprise the step of fixing the trajectory of the drill bit with respect to the bone plate. The step of drilling a hole with the drill bit may comprise moving the drill bit through the fastener hole.

The method may comprise using a drill bit having at least one depth marking, wherein step (c) further comprises selecting a drilling depth by sliding the adjustable depth stop assembly to a position adjacent the depth marking. The method may also comprise associating the housing with the bone segment prior to the step of adjusting the axial position of the depth stop assembly along the drill bit to position the housing a first distance from the depth stop assembly.

BRIEF DESCRIPTION OF THE DRAWINGS

For a better understanding of the nature and objects of the invention, reference should be made to the following detailed description, taken in conjunction with the accompanying drawings, in which:

FIG. 3A is a side view of the adjustable depth drill bit of FIG. 1;

FIG. 3B is a expanded view of a portion of the adjustable depth drill bit of FIG. 1;

FIG. 15 shows the adjustable depth stop of the adjustable depth drill bit of FIG. 1; and FIG. 16 is a cross-sectional side view of the adjustable depth stop of the adjustable depth drill bit of FIG. 1.

Like reference numerals refer to corresponding parts throughout the several views of the drawings.

DETAILED DESCRIPTION OF THE INVENTION

Figure 1:
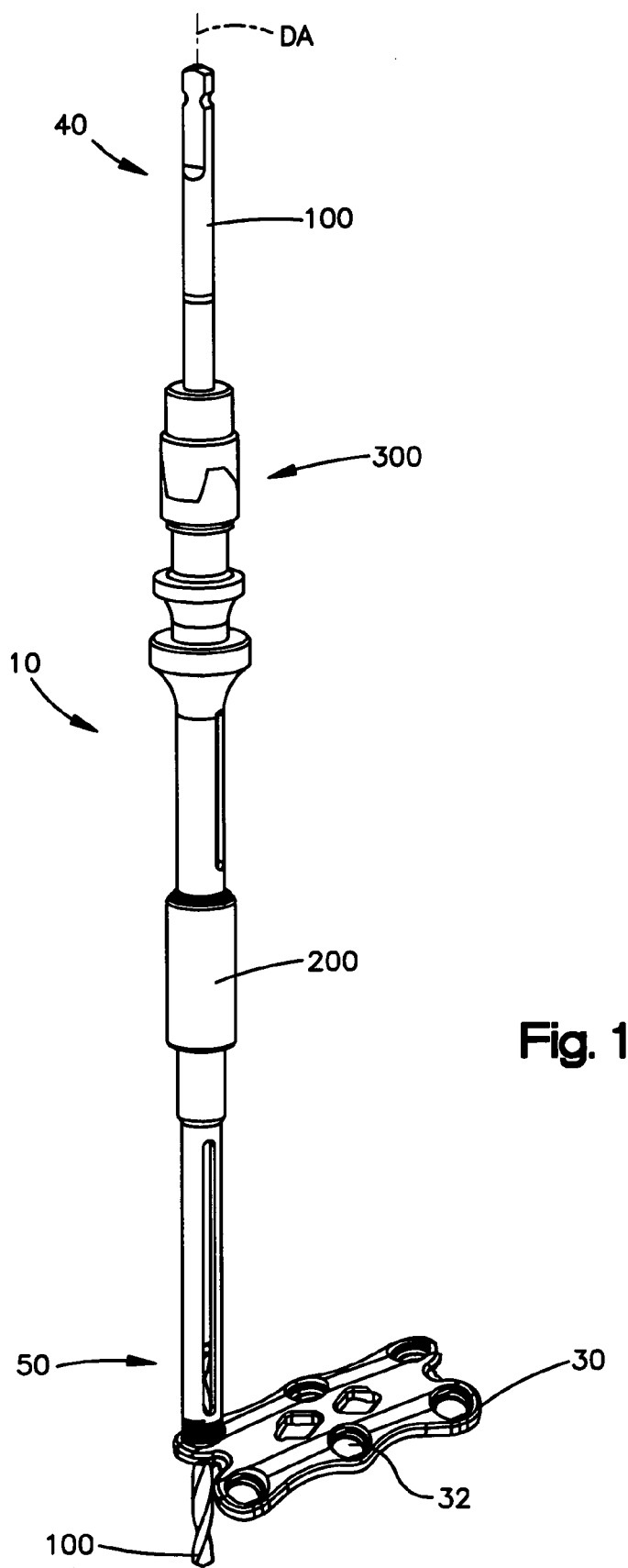
FIG. 1 is a perspective view of an adjustable depth drill bit attached to a bone plate according to one embodiment of the present invention.

Referring to FIG. 1, there is shown an exemplary drill assembly 10, which may be adapted for use with a fixation device, such as for example, a spinal fixation plate 30. While the drill assembly is disclosed in conjunction with a spinal fixation plate it is contemplated that the drill assembly may be used in conjunction with bone fixation plates used on or in any portion of the body. The drill assembly may be used with metal fixation plates as well as with bio-resorbable, polymer based, or any other bone fixation plates known in the art. Drill assembly 10 may include a drill bit 100 having a proximal end 40, a distal end 50 and a longitudinal axis 20. Drill assembly 10 also may include a housing assembly 200, and an adjustable depth stop assembly 300 each disposed along the length of the drill bit 100. The housing assembly 200 may be configured to orient and fix the drill bit with respect to the bone plate and bone (i.e. it may fix the drill trajectory), while the adjustable depth stop assembly 300 may comprise the depth adjustment mechanism of the device which may permit the user to pre-select the ultimate drilling depth into bone. The housing assembly 200 and the adjustable depth assembly 300 may comprise corresponding stop surfaces 258, 322 that may cooperate to limit axial travel of the drill bit 100, thereby limiting the drilling depth.

In general, to operate the adjustable depth drill bit 10, a surgeon or 'user' determines the drilling depth desired for a particular procedure, which typically depends upon the length of screw selected for implantation. The user then may adjust the position of the adjustable depth stop 300 along the length of the drill bit 10 (described in more detail below) to provide the desired movement allowance of the drill bit 100, as indicated by measured markings 110 on the drill bit 100. Next, the distal end 220 of the housing 200 may be positioned within a selected screw hole 32 of the bone plate 30.

Engaging the screw hole may serve to align the drill bit 100 along the appropriate drilling trajectory such that the bone screw hole (and thus the screw that will ultimately be driven into the hole), will assume the desired angular positioning with respect to the plate and the bone. Once drilling is begun and the drill is moved distally into the bone, the adjustable depth stop 300 automatically limits the total travel of the drill bit to the selected depth without further action from the user.

Figure 2:
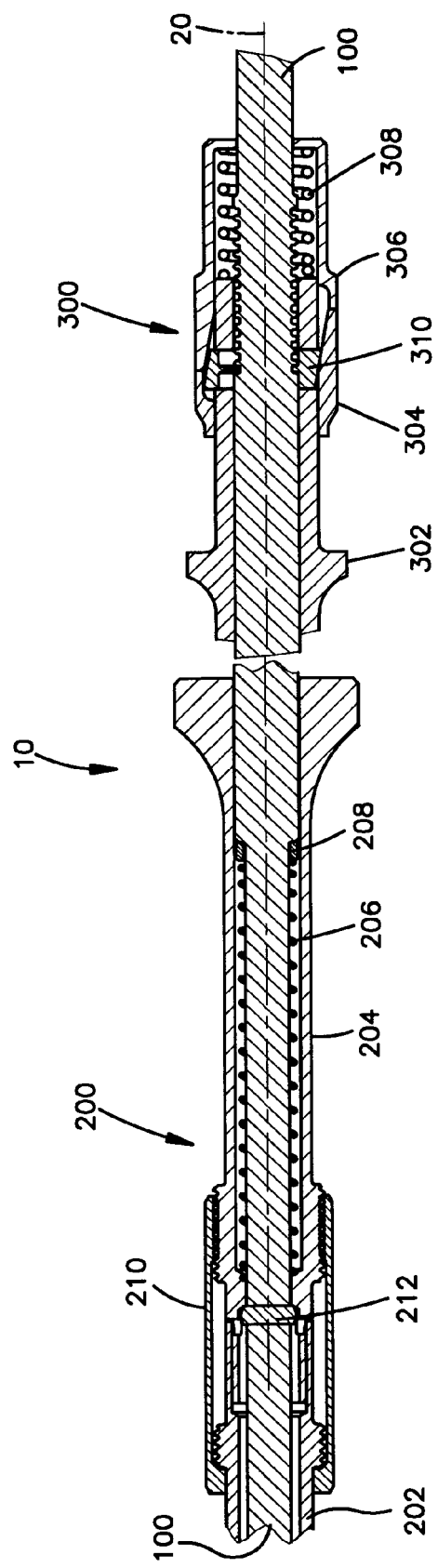
FIG. 2 is a cross-sectional side view of the adjustable depth drill bit of FIG. 1.

FIG. 2 shows a truncated cross-section of the adjustable drill assembly 10 of FIG. 1. Drill bit 100 is shown as defining a longitudinal axis "DA." Housing assembly 200 may generally comprise a distal housing portion 202, a proximal housing portion 204 having an stop surface 258 for engaging the adjustable depth stop assembly 300, a compression spring 206, a washer 208, a threaded retainer 210, and a bushing 212. Adjustable depth stop assembly 300 may generally comprise a shuttle sleeve 302 having a stop surface 322 for engaging stop surface 258 of the housing assembly 200, a locking sleeve 304, a removal sleeve 306, a biasing spring 308, and a sliding shuttle 310.

As previously noted, the housing assembly 200 may function to align the drill bit within a targeted bone screw hole. The housing assembly may also serve as a protective cover for the drilling flutes of the drill bit 100 when the assembly is not in use, and may further serve as a gripping element to allow manipulation and installation of the device on the bone plate. The housing assembly 200 may comprise a bone plate engaging surface 222 at its distal end 220 (see FIG. 4), which in the illustrated embodiment may comprise threads configured to mate with a correspondingly threaded bone screw hole of a bone plate 30. Housing assembly 200 may also be configured to axially retain the drill bit between a fully recessed position and a fully extended position. In the fully recessed position, the distal end 104 of drill bit 100 may be contained within the housing 200 so that no portion of the drill bit extends beyond the housing distal end. In the fully extended position, the drill bit distal end 104 may extend beyond the distal end of the housing to engage a bone surface underlying a bone plate.

The housing may have a reduced diameter shoulder region 241 configured to axially engage a pin 212 positioned transversely through drill bit shaft 111, thus preventing the drill from moving distally out of engagement with the housing. A spring 206 may be positioned within housing 200 and over a portion of the drill bit 100. The spring 206 may have a proximal end 207 associated with a proximal shoulder 108 of the drill bit 100 and a distal end 209 positioned against a distal shoulder 253 of the housing 200. When assembled, the spring 206 may axially bias the drill bit 100 in the proximal direction. A bushing 208 may be interposed between the proximal end of the spring 207 and the proximal shoulder 108 of the drill bit to protect the spring 206 from binding with the turning drill bit 100 during drilling. Thus, the bushing 208 may be press-fit into the housing 200 and may remain stationary when the drill bit 100 turns. This bushing 208 may be made of metal, polymer (e.g. Teflon, Polyether-ether-ketone (PEEK), etc.), or any other material known in the art to be suitable for such use.

Spring 206 and pin 212 thus may act to maintain the drill bit 100 in an initial "neutral" position in which the drill bit 100 is recessed within the distal end of the housing when not in use (the pin 212 acting to prevent the spring 206 from moving the drill bit too far in the proximal direction). To extend the drill bit from the housing in use, the user may apply a distal axial force to the drill bit sufficient to overcome the biasing force of the spring. When the distal axial force is removed (e.g., when drilling is complete), the bias of the spring 206 once again may cause the drill bit 100 to recede fully within the distal end of the housing.

In order to adjust the device to achieve the desired drilling depth, the user may adjust the allowable length of travel of the drill bit 100 through the housing 200 by using the adjustable depth stop assembly 300, which may be selectively positionable along the length of the drill bit 100. This selective positioning may be accomplished by sliding shuttle 310, which may be axially retained within the depth stop assembly 300, and which may have a surface that is selectively engageable and disengageable with a series of measured recesses 112 in the body of the drill bit 100. The sliding shuttle 310 may slidingly engage a pair of tapered surfaces 334, 344 on the locking and removal sleeves 304, 306 such that moving the sleeves axially with respect to the shuttle may cause the shuttle to translate laterally with respect to the drill bit, thus moving the shuttle into, or out of, engagement with one of the drill bit recesses 112 (as will be described in more detail later). When the sliding shuttle 310 is disengaged from the drill bit recesses 112, the adjustable depth stop may be moved axially along the drill bit 100. Likewise, the adjustable depth stop may be fixed in a desired axial position by re-engaging the sliding shuttle 310 with the appropriate drill bit recesses 112. In this manner, the distance between the stop surfaces 258, 322 of the proximal housing 204 and the shuttle sleeve 302, respectively, may be adjusted. Since the housing 200 is fixed to the bone plate and the depth stop assembly 300 is fixed axially to the drill bit 100, the distance between the housing and the depth stop assembly is equal to the total amount of distal travel afforded the drill bit 100. Thus, the drilling depth is controlled by controlling the distance between the housing 200 and the depth stop assembly 300.

In use, the surgeon may select the desired drilling depth by adjusting the distance between the two assemblies as described above, as measured by the markings 110 on the exterior of the drill bit 100 (FIG. 3A). This adjustment may be made either before or after the device is engaged with the bone plate. When drilling is commenced, the surgeon may apply an axial force to the drill bit to drive it distally into contact with the bone, thereby moving the drill bit out and away from the distal end of the housing. As previously noted, since the depth stop assembly moves axially with the drill bit and the housing assembly remains fixed to the plate, the total travel of the drill bit—and thus the drilling depth— is limited (i.e. stopped) when the distal end stop surface 322 of the adjustable drill stop assembly 300 contacts the stop surface 258 of the proximal housing 204.

Referring now to FIG. 3A, the drill bit 100 will be discussed in detail. Drill bit 100 may have proximal and distal ends 102, 104, and a longitudinal axis 20. The distal end of drill bit 100 may include drill flutes 106, which can be standard drill flutes commonly used for drilling. Drill bit 100 can also be any other appropriate type of boring arrangement, such as for example, a needle, an awl, a punch, a burr, a reamer, or the like, provided the arrangement is configured to produce a desired opening or pilot hole of desired depth in the underlying bone for insertion of bone screws or other fastening elements. Drill bit 100 may also include a stop 108, which may be formed by an increased-diameter portion 109 of drill bit 100. Stop 108 may act as a retainer for washer 208, described in more detail below, and may also provide a bearing surface for compression spring 206 which biases the drill bit 100 in the proximal direction to maintain the distal portion of the drill bit within the distal housing 202 when not in use. Drill bit 100 also may include one or more depth markings 110 arranged along at least a portion of its length, and these depth markings may correspond to a maximum distance which distal end 104 of drill bit 100 may protrude from housing 200 during drilling, as will be described in more detail below. Positioned along at least a portion of the drill bit length at a corresponding distance from depth markings 110, and in increments equidistant to the depth markings 110, are circumferential lock grooves 112. Lock grooves 112, shown in more detail in FIG. 3B, may be configured to receive a locking tab, such as a lock ridge 368 (FIG. 14) of sliding shuttle 310 of the adjustable depth stop 300 (further described below). In one embodiment there may be one or more lock grooves 112 spaced apart from each other by a distance "d." In the illustrated embodiment, there are fourteen lock grooves 112, each spaced apart from each other by a distance "d" of about 1 millimeter (mm), such that the drilling depth of drill bit 100 can be adjusted in increments of about 1 mm. It is noted that the lock grooves 112 may be spaced apart by any appropriate distance "d," to provide a desired incremental adjustment in maximum drilling depth. In one embodiment the lock grooves 112 themselves may each have a width "w" of about 0.55 mm and a height "h" of about 0.5 mm. The lock grooves 112 may taper outward, widening the lock groove 112 thickness toward the outer edge of the lock groove 112 for easier reception of the lock ridge 368 of the sliding shuttle 310 (further described below).

Returning to FIG. 3A, the proximal end 102 of drill bit 100 may have a coupling surface 115 configured for quick release attachment to a suitable drill handpiece (not shown) which may be either a manual or externally powered device. The coupling surface 115 can include, as shown in FIG. 3A a flat surface 114 on one side of drill bit 100 and a coupling groove 116 for releasably retaining drill bit 100 within the handpiece, although any suitable coupling arrangement may be used.

In one embodiment, drill bit 100 may be about 240 mm in length from proximal end 102 to distal end 104. The drill flutes 106 may extend about 34 mm from the distal end 104 toward the proximal end 102. The diameter of drill bit 100 at the drill flutes 106 may be about 3.0 mm and may increase to about 3.5 mm over a longitudinal span of about 0.5 mm at about 35 mm from the distal end 104. The diameter of drill bit 100 may increase further to about 5.2 mm over a longitudinal span of about 0.5 mm, forming stop 108, at a distance of about 120 mm from the distal end 104.

Figure 4:
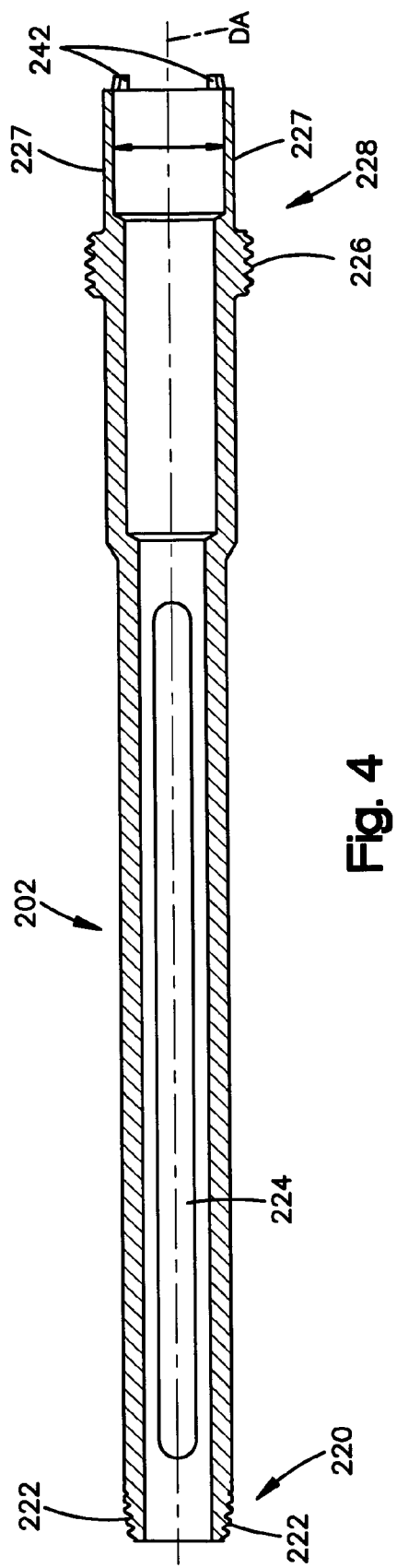
FIG. 4 is a cross-sectional side view of the distal housing of the adjustable depth drill bit of FIG. 1.

FIG. 4 shows distal housing 202 configured to encompass at least a portion of distal end 104 of drill bit 100 to guide the drill bit 100 along the desired trajectory relative to the bone plate 30 and bone screw hole 32. Distal housing 202 may be a generally cylindrical housing defining a open or hollow central bore having a variable inner diameter configured to mate with corresponding variable outer diameters of the drill bit 100 and dimensioned to be slightly larger than the outer diameters of the mating portions of the drill bit 100 so that the drill bit may slide and rotate freely therein. The distal-most end 220 of distal housing 202 is configured to engage a bone screw hole 32 of bone plate 30. In one embodiment, the distal-most end 220 may comprise tapered threads 222 configured to correspond and engage matching inner threads of at least one bone screw hole of bone plate 30. In an alternative embodiment, the distal most end 220 may comprise a smooth taper configured to match a smooth or threaded taper of at least one bone screw hole of the bone plate 30. In a further embodiment, the taper angle of the distal most end 220 may be greater than, or less than, that of the bone screw hole. Any appropriate taper angle may be provided for the distal most end 220 as long as it allows the distal housing 202 to be aligned within the bone screw hole. Such alignment ensures the hole drilled into the bone may have the same trajectory as that of the bone screw hole, thus ensuring the associated bone screw will properly engage the bone screw hole when installed.

Distal housing 202 may further comprise a visualization slot 224 extending longitudinally along at least a portion of its length. Visualization slot 224 may function to provide a user with a window to see at least a portion of drill bit 100 within the distal housing during operation. This slot also may provide for easier cleaning and sterilization of the device after use, and may further provide an exit path for material removed by the drilling flutes during operation. The visualization slot 224 may be about 2 mm in width and about 45 mm in length. In an alternative embodiment, two or more visualization slots 224 may be provided on distal housing 202. Distal threads 226 may be provided near the proximal end 228 of the distal housing 202 to facilitate engagement of the distal housing with the proximal housing 204 and the threaded retention sleeve 210, as will be described below.

Figure 5:
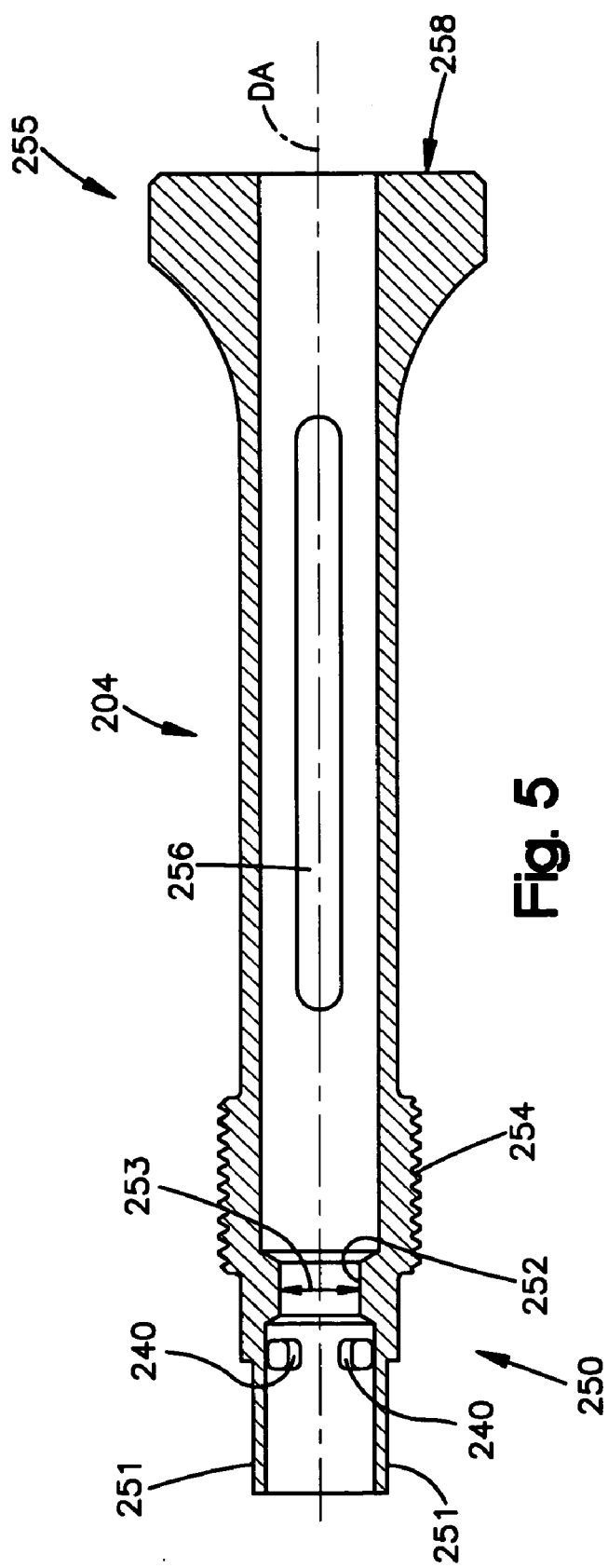
FIG. 5 is a cross-sectional side view of the proximal housing of the adjustable depth drill bit of FIG. 1.

As shown in FIGS. 4 and 5, the proximal most end 228 of distal housing 202 may include a set of alternating recesses 242 and protrusions 243. When assembled with proximal housing 204, the recesses 242 and protrusions 243 of the distal housing 202 may interlock with corresponding protrusions 240 and recesses 245 of the proximal housing 204. The interlocking of the corresponding recesses 242, 245 and protrusions 240, 243 of the two housing segments may allow the two housings to transmit torque between them following assembly.

FIG. 5 shows the proximal housing 204 in greater detail. Distal end 250 of proximal housing 204 may be configured to mate with the proximal end 228 of distal housing 202 through interaction of the recesses/protrusions 242, 243 of the distal housing 202 with the locking protrusions/recesses 240, 245 of the proximal housing 204, respectively. Furthermore, distal housing 202 includes distal sleeve element 227 at its proximal end 228 which is configured to receive proximal sleeve element 251 of the distal end 250 of proximal housing 204. The outer diameter of proximal sleeve element 251 may be slightly smaller than the inner diameter of distal sleeve element 227 such that when distal and proximal housing 202, 204, respectively are mated, proximal sleeve element 251 may fit within distal sleeve element 227.

Proximate to the distal end 250 of the proximal housing is a reduced-diameter throat portion 252 having an inner diameter 253 which may act as a guide for drill bit 100, maintaining drill bit 100 in alignment with longitudinal axis 20 of the proximal and distal housings. In one embodiment, the inner diameter 253 of the throat portion 252 may be slightly larger than the outer diameter of the drill bit 100 such that the drill bit 100 can freely axially rotate and longitudinally translate within throat portion 252 while maintaining alignment with the longitudinal axis 20 of the housings. Proximal housing 204 may further comprise an externally threaded section 254 disposed adjacent the housing distal end 250, and these threads may further be configured to mate with inner threads 270 of threaded retainer 210 (FIG. 6).

Proximal housing 204 may further include a longitudinal visualization slot 256. As previously described with respect to visualization slot 224 on the distal housing 202, longitudinal slot 256 of the proximal housing 204 may be configured to allow the user to view the proximal portion of the drill bit 100 during use. Likewise, the slot 256 may also provide for easier cleaning and sterilization of the device after use, and may also provide an exit path for material removed by the drilling flutes during operation. The proximal most end of the proximal housing 204 may comprise a flared portion 255 suitable for gripping by the user. The flared portion 255 may have a stop surface 258 on the proximal end thereof, the stop surface 258 configured to engage stop surface 322 of shuttle sleeve 302 when the drill bit 100 reaches a maximum set drill depth. The perimeter of flared portion 255 may further include a knurling or other surface texturing or roughening to facilitate user application of a rotational force to the proximal housing 204 to couple the distal portion of the housing 200 with bone plate 30 once the proximal housing 204 and the distal housing 202 have been assembled as described.

Figure 6:
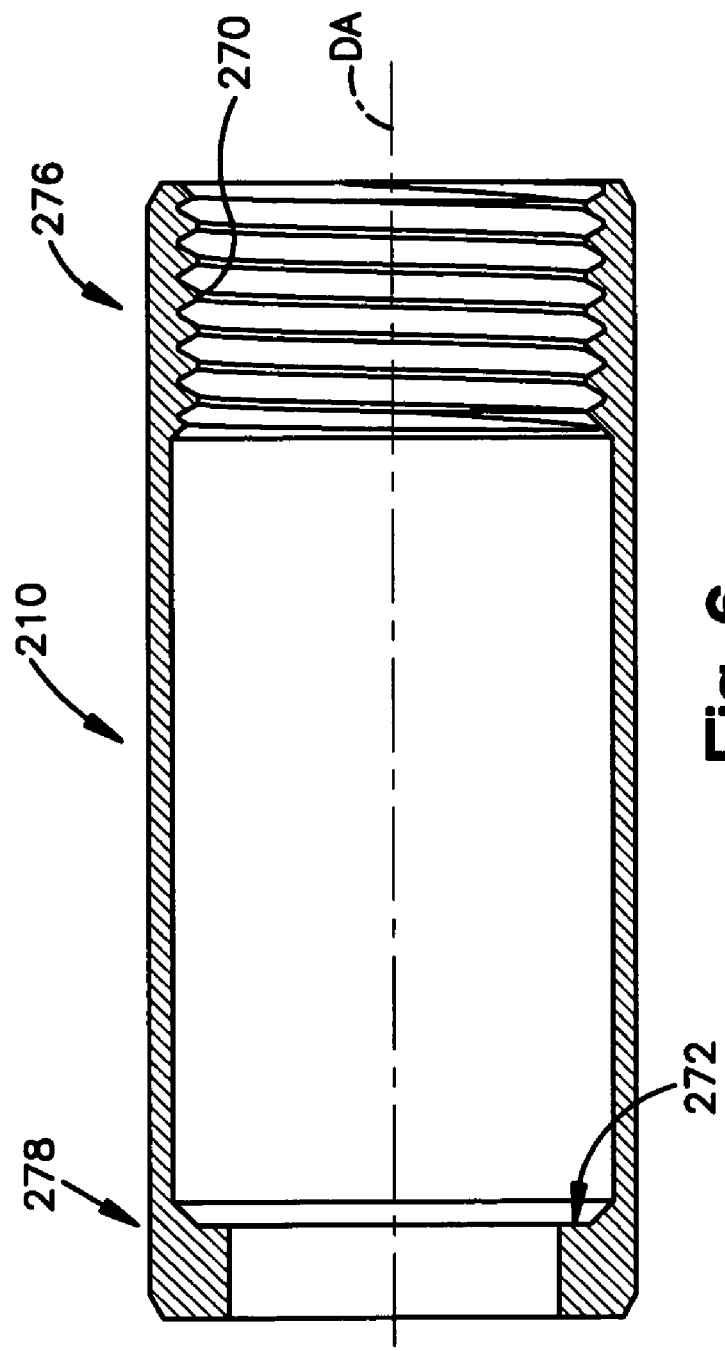
FIG. 6 is a cross-sectional side view of the threaded retainer of the adjustable depth drill bit of FIG. 1.

Referring now to FIG. 6, threaded retainer 210 is shown in more detail. In use, threaded retainer 210 may be used to fix the distal and proximal housings 202, 204 together. An internally threaded section 270 may be provided at the proximal end 276 of the retainer 210, and this threaded section 270 may be configured to threadably accept the externally threaded sections 226, 254, on the distal and proximal housings 202, 204, respectively. These threaded connections may be provided to facilitate fit-up of the housing sections to enable the entire assembly to be disassembled after use for easy cleaning and sterilization. Thus, although the retainer and proximal and distal housings are disclosed as comprising threaded connections, these pieces may be connected using any suitable removable couplings or connections in the art.

To assemble the proximal and distal housings 202, 204, threaded retainer 210 may be positioned so that its proximal threaded end 276 is placed over the distal end 220 of distal housing 204 and slid toward the housing proximal end 228. Once the retainer has been slid sufficiently far that threads 270 of the threaded retainer 210 engage the distal threads 226 of the distal housing, the retainer 210 may then be rotated until the internal threads 270 of the retainer pass through and out of engagement with the external threads 226. The retainer 210 is thus loosely and slidably retained on the distal housing 202. The proximal housing 206, with drill bit 100 and spring 206 pre-installed therein, may then be engaged with the distal housing 202. The sleeve elements 251, 227 and respective protrusions and recesses 242, 243, 240, 245 of the distal and proximal housings 202, 204, may then be engaged to align the housings along the longitudinal axis 20. The two housings 202, 204 then may be axially fixed together by engaging the proximal threads 270 of the retainer 210 with external threaded section 254 located adjacent the distal end 250 of the proximal sleeve 204. As the retainer 210 translates along the proximal threads 270, the reduced diameter lip 272 formed at the distal end 278 of the threaded retainer 210 engages the threaded proximal portion 226 of the distal housing 202, pulling the distal housing 202 toward the proximal housing 204 and pressing the housings together.

In order to adjust the device to achieve the desired drilling depth, the user may adjust the allowable length of travel of the drill bit 100 through the housing 200 by using the adjustable depth stop assembly 300, which may be selectively positionable along the length of the drill bit 100. This selective positioning may be accomplished using a sliding shuttle 310, which may be axially retained by the depth stop assembly 300, and also may be selectively engageable and disengageable with a series of measured recesses 112 in the body of the drill bit 100. Thus, the sliding shuttle 310 may act to selectively axially lock and unlock the depth stop assembly 300 and the drill bit 100. The sliding shuttle 310 may be laterally movable with respect to the longitudinal axis "DA" of the depth stop assembly 300 and the drill bit 100 when the latter is inserted into the former. The lateral position of the sliding shuttle 310 may be controlled using the removal and locking sleeves 306, 304 which are slidably mounted on shuttle sleeve 302, and which may comprise opposing parallel planar surfaces 334, 344 against which the sliding shuttle 310 may slide during operation. These parallel planar surfaces 334, 344 may form an oblique angle α (FIGS. 9 & 11) with respect to the longitudinal axis "DA" of the depth stop assembly 300, and the sliding shuttle 310 may have first and second tapered end surfaces 374, 376 which are angled to mate with respective parallel planar surfaces 334, 344. When the removal and locking sleeves 306, 304 are slid axially along the shuttle sleeve 302, the interaction between the angled surfaces 334, 344 of the sleeves and the correspondingly angled ends 374, 376 of the sliding shuttle 310 may cause the shuttle 310 to move laterally within the slot 342. This lateral movement may cause lock ridge 368 of sliding shuttle 310 (FIGS. 13 & 14) to engage or disengage one of the corresponding recesses 112 in the drill bit 100, depending upon whether the locking/removal sleeves 304, 306 are moved in the proximal or distal direction with respect to the shuttle sleeve 302. Thus, sliding the locking/removal sleeves 304, 306 proximally along the shuttle sleeve 302 may cause the sliding shuttle 310 to engage one of the drill bit grooves 112, while sliding the locking/removal sleeves distally along the shuttle sleeve may cause the sliding shuttle to disengage the drill bit groove.

When the sliding shuttle 310 is disengaged from the drill bit recesses 112, the adjustable depth stop may be free to move along the length of the drill bit 100. Likewise, the adjustable depth stop may be fixed in a desired axial position by re-engaging the sliding shuttle 310 with the appropriate drill bit recess 112. In this manner, the distance between the engaging surfaces 258, 322 of the proximal housing 204 and the shuttle sleeve 302, respectively, may be adjusted, and it is this distance which may ultimately control the amount of distal travel afforded the drill bit 100. The drill bit 100 is axially movable with respect to the housing 200 and may be axially fixed to the depth stop assembly 300 as previously described. In operation, as the user applies a distal axial force to the drill bit 100 to move it into contact with the bone, the depth stop assembly 300 travels along with the drill bit. When the distal end of the depth stop assembly 300 engages the proximal end of the housing 200, further distal movement of the depth stop assembly 300 and drill bit 100 is prevented, and the drilling depth is thusly limited.

Figure 7:
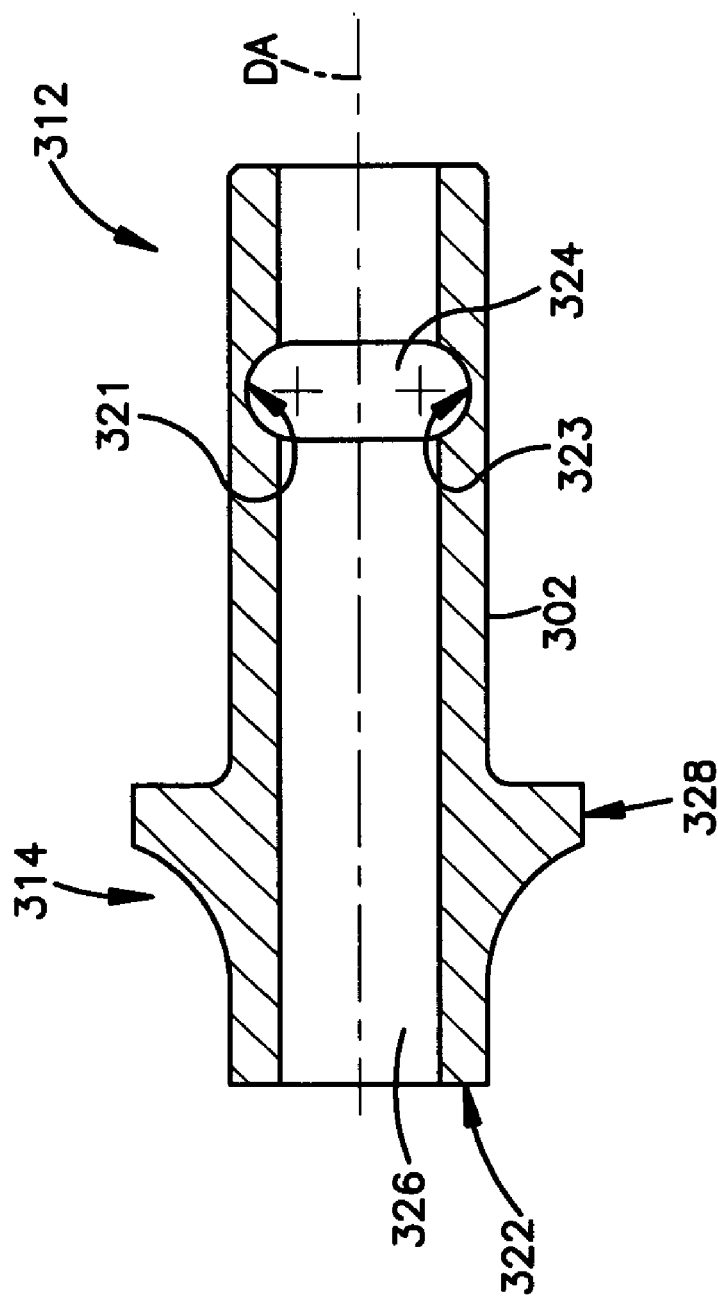
FIG. 7 is a cross-sectional side view of the shuttle sleeve of the adjustable depth drill bit of FIG. 1.
Figure 13:
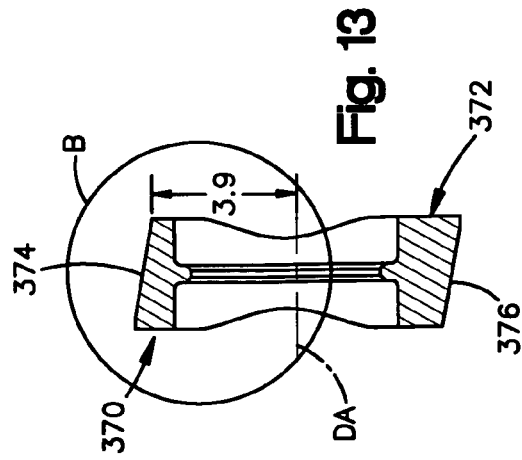
FIG. 13 is a cross-sectional view of the sliding shuttle of the adjustable depth drill bit of FIG. 1.

FIG. 7 shows a longitudinal cross-section of shuttle sleeve 302 which may have proximal and distal ends 312, 314, respectively, and a longitudinal axis "DA." The shuttle sleeve 302 may have a central bore 326 oriented coaxial with the longitudinal axis "DA" of the shuttle sleeve 302. The central bore 326 may be sized to slidingly receive drill bit 100, thus allowing the shuttle sleeve 326 to move axially along the drill bit 100. Shuttle sleeve 302 may include a shuttle slot 324, which may be configured to slidably receive sliding shuttle 310 (FIG. 13). Shuttle slot 342 may have an axis substantially perpendicular to the longitudinal axis "DA" of shuttle sleeve 302, so that the sliding shuttle 310 may slide within the slot 342 in a direction transverse to the shuttle sleeve bore 326 (and thus the drill bit 100). In the illustrated embodiment, shuttle slot 324 may have a substantially rectangular or elongated central cross section with rounded ends 321, 323. This elongated cross section may be provided to prevent the sliding shuttle 310 from rotating within the slot 324 during use. It is noted that the shuttle slot 324 may be provided with any appropriate geometric cross section (e.g. rectangular, square, triangular, round, elliptical, etc.) provided it may configured to mate with the cross section of the sliding shuttle to prevent the shuttle from rotating within the slot. Shuttle slot 324 may extend completely through two opposing lateral sides of shuttle sleeve 302 such that sliding shuttle 310—when positioned within the slot 324—may laterally protrude from either side of the sleeve 302.

Shuttle sleeve 302 may further comprise a stop surface 322 at its distal end configured to engage a corresponding stop surface 258 of the distal housing 200 during operation. The shuttle sleeve may also have an increased diameter flange portion 328 located adjacent the sleeve distal end 314, the flange portion 328 being configured to allow grasping of the shuttle sleeve 302 by a user during operation.

Figure 9:
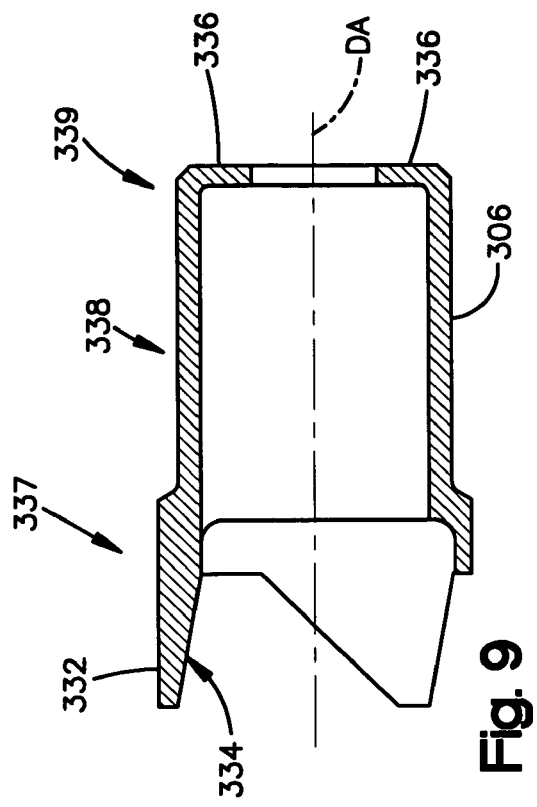
FIG. 9 is a cross-sectional side view of the removal sleeve of the adjustable depth drill bit of FIG. 1.
Figure 8:
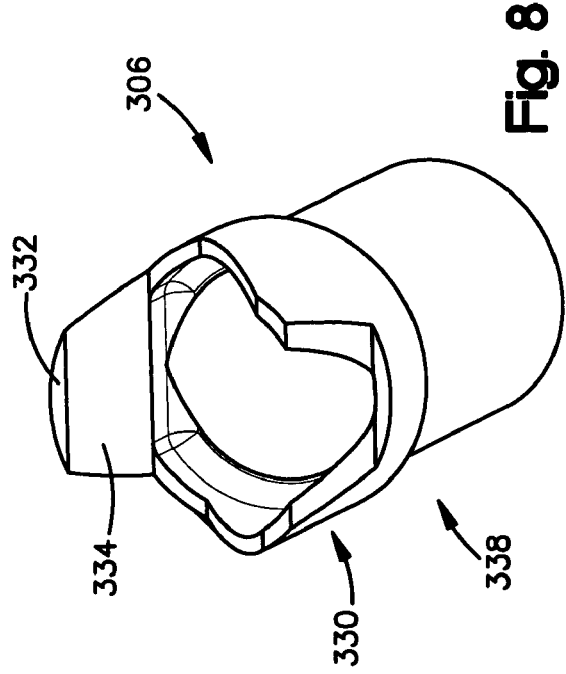
FIG. 8 is a perspective view of the removal sleeve of the adjustable depth drill bit of FIG. 1.

FIGS. 8 and 9 show the removal sleeve 306, which, in operation, may cooperate with the locking sleeve 304 (FIGS. 10 & 11) to control the lateral position of sliding shuttle 310 within the shuttle slot 324 of the shuttle sleeve 302, thus controlling the locking and unlocking of the depth stop assembly 300 with the drill bit 100.

When assembled on shuttle sleeve 302, removal sleeve 306 may share a common longitudinal axis "DA" with drill bit 100, shuttle sleeve 302, and locking sleeve 304. Removal sleeve 306 may comprise a reduced diameter proximal portion 339, an intermediate portion 338 and a distal portion 337. The reduced diameter proximal end 339 may have a lip 336 sized to slidingly accept the drill bit 100, and the intermediate portion 338 may be sided to slidingly accept the proximal end 312 of shuttle sleeve 302.

The distal portion 337 of removal sleeve 306 may be configured to engage the proximal portion 340 of locking sleeve 304 (see FIGS. 8 and 9), to axially and rotationally lock the two sleeves together during use. Thus, the distal portion of removal sleeve 306 may comprise at least one axially extending engagement tab 332, configured to engage a corresponding proximal recessed portion 343 of the locking sleeve 304. Likewise, the removal sleeve 306 may comprise at least one distal recessed portion 333 configured to engage an axially extending engagement tab 342 of the locking sleeve 304.

Figure 11:
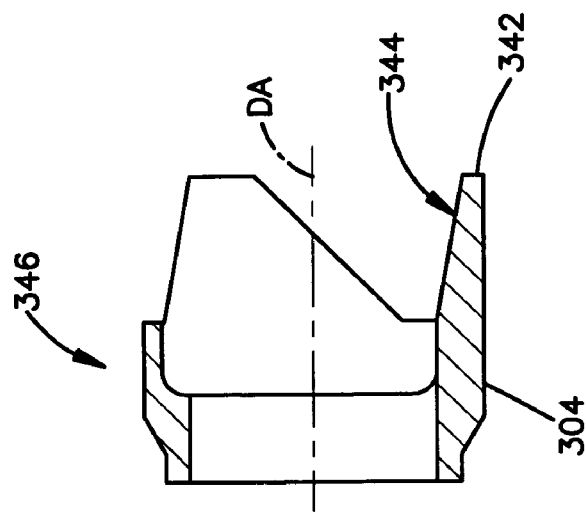
FIG. 11 is a side view of the locking sleeve of the adjustable depth drill bit of FIG. 1.
Figure 10:
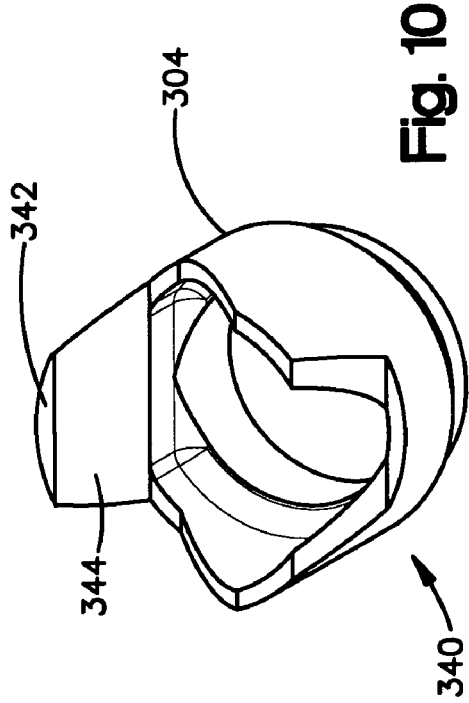
FIG. 10 is a perspective view of the locking sleeve of the adjustable depth drill bit of FIG. 1.

FIGS. 10 and 11 show the locking sleeve 304 having proximal and distal portions 345, 347. The proximal portion 345 may be configured to engage the distal portion 337 of removal sleeve 306 as previously described, and the distal portion 347 of locking sleeve 304 may be sized to slidingly receive the proximal end 312 of shuttle sleeve 302. When assembled on shuttle sleeve 302, removal sleeve 306 may share a common longitudinal axis "DA" with drill bit 100, shuttle sleeve 302, and removal sleeve 304.

As previously mentioned, the engagement tabs 332, 342 of the removal and locking sleeves 302, 304 may cooperate with locking sleeve 304 to control the lateral position of the sliding shuttle 310 within the shuttle slot 324, thus controlling the locking and unlocking of the depth stop assembly 300 with the drill bit 100. As such, the engagement tabs 332, 342 each have a tapered shuttle engaging surface 334, 344 (FIGS. 9 & 11) which may be configured to slidingly engage corresponding tapered end surfaces 374, 376 of the sliding shuttle 310. The tabs 332, 342 may be configured and oriented on the removal and locking sleeves 302, 304 so that when the sleeves are fit together, the tabs are diametrically opposed, which may result in the respective tapered shuttle engaging surfaces 334, 344 being parallel (see FIG. 15).

The tapered shuttle engaging surfaces 334, 344 may each be configured to form an acute angle a that is oblique to the longitudinal axis "DA" of the locking and removal sleeves 304, 306. The angle a may be selected from the range of from about 1 degree to about 45 degrees. In the illustrated embodiment, α is about 10 degrees.

In the illustrated embodiment, engagement tab 332 tapers from a thick portion near the locking sleeve intermediate portion 338 to a narrower portion nearer the sleeve distal end 337. Likewise, engagement tab 342 tapers from a narrow portion near the removal sleeve proximal end 345 to a thicker portion near the sleeve distal end 347.

Figure 14:
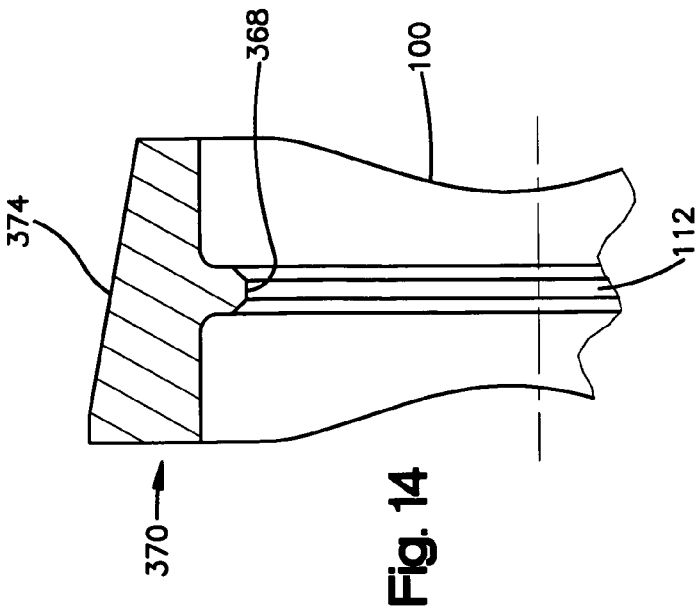
FIG. 14 is an expanded partial cross-sectional view of the sliding shuttle of the adjustable depth drill bit of FIG. 1.
Figure 12:
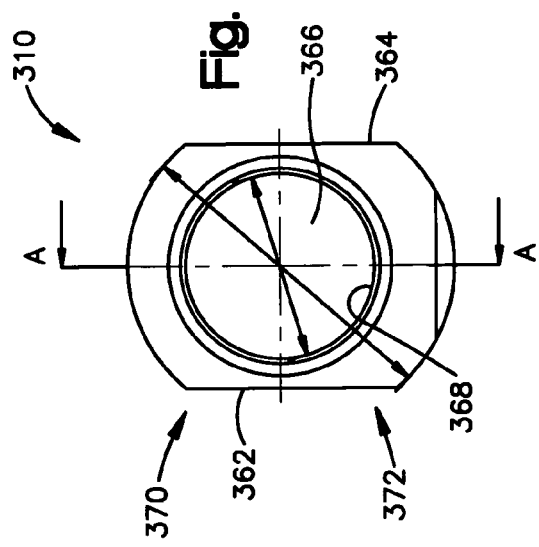
FIG. 12 is a top plan view of the sliding shuttle of the adjustable depth drill bit of FIG. 1.

Referring now to FIGS. 12–14, the sliding shuttle 310 will now be described. As illustrated in FIG. 12, the sliding shuttle 310 may be a generally washer-shaped element having two generally flat parallel side portions 362 and 364. Sides 362, 364 may be configured to be slidably receivable within corresponding surfaces 321, 323 of shuttle slot 324 (FIG. 7). Offset from the center of the sliding shuttle 310 may be a bore 367 having a bore axis "BA" and an inner surface portion 366. The bore 367 may be configured to have a diameter larger than the outer diameter of the drill bit 100. Disposed within at least a portion of the circumference of the inner surface portion 366 is a lock ridge 368. Lock ridge 368 may protrude radially inward from the inner surface portion 366 toward the center of the bore 367. Lock ridge 368 further may be configured to mate with lock grooves 112 of drill bit 100 when the drill bit is inserted into the bore 367 and the sliding shuttle 310 is pressed laterally against one of the lock grooves 112. The inner surface portion 366, including lock ridge 368 may have an inner diameter "ID" that is greater than the outer diameter of the drill bit 100. Thus, when the drill bit 100 is substantially centered within the inner surface portion 366 of the sliding shuttle 310, the drill bit 100 and sliding shuttle 310 may be free to slide axially with respect to each other. Likewise, when the sliding shuttle 310 is moved laterally with respect to this center position, lock ridge 368 may engage one of the grooves 112 in the drill bit 100 to axially fix the sliding shuttle 310 and drill bit 100 together.

Referring to FIGS. 12, 13 and 14, tapered end surfaces 374, 376 each may form an angle α with respect to the bore axis "BA," and with axis "DA" when the device is fully assembled. As previously indicated, these tapered end surfaces 374, 376 are configured to correspond to tapered surfaces 334, 344 of the removal and locking sleeves, respectively.

Because the bore axis "BA" is offset from the central axis "SA" of the sliding shuttle 310, the distance from the bore axis "BA" to the outer periphery of tapered surfaces 374, 376 differs. For ease of reference, the side of the shuttle comprising tapered engaging surface 374 will be referred to as "short side 370" and the side of the shuttle comprising tapered engaging surface 376 will be referred to as "long side 372." In the illustrated embodiment, the portion of lock ridge 368 adjacent the long side 372 of the sliding shuttle engages a respective drill bit groove 112 when the sliding shuttle 310 is located adjacent the distal-most portion of locking sleeve tapered surface 344, as shown in FIG. 2

When the locking/removal sleeves 304/306 are moved distally along the shuttle sleeve 302 so as to position the sliding shuttle adjacent the proximal-most portion of the removal sleeve tapered surface 334, the sliding shuttle 310 is laterally translated so that the long side 372 is moved laterally away from the drill bit 100 (disengaging the shuttle from the grooves) and the short side 370 is moved laterally toward the drill bit. When the short side 370 of the sliding shuttle 310 is fully translated toward the drill bit 100, its extension may not be sufficient to allow the portion of lock ridge 368 located adjacent the short side 370 to engage one of the drill bit grooves 112

To assemble the adjustable depth stop assembly, locking sleeve 304 may be slid over the proximal end of sliding shuttle 310 and moved to a position distal of the shuttle slot 324. The sliding shuttle 304 may then be inserted within shuttle slot 324 of shuttle sleeve 302 such that short side 370 and long side 372 of the sliding shuttle 310 both extend slightly beyond the outer circumference of shuttle sleeve 302, as shown in FIGS. 2 and 16. Next, biasing spring 308 may be placed within the bore of the removal sleeve 306, and the two pieces may be slid over the proximal end of shuttle sleeve 302. The locking sleeve 304 and removal sleeve 306 may then be rotatably adjusted so that their complementary tabs 342, 332 may engage with respective recesses 333, 343 on the other sleeve, and so that the shuttle sleeve 302 may be properly engaged with the tapered inner surfaces 344, 334 of sleeves 304, 306 respectively. In particular, the inner surface 334 taper of sliding shuttle engagement tab 332 may engage the short side taper 374 and the tapered inner surface 344 of the sliding shuttle engagement tab 342 may engage the long side taper 376, see FIG. 16. The locking and removal sleeves 304, 306 may then be fixed to one another using any appropriate fixation arrangement (e.g. laser welding, brazing, adhesive, etc.). FIG. 2 shows the assembled adjustable drill stop 300, including the removal sleeve 306, locking sleeve 304, sliding shuttle 310, and shuttle sleeve 302 engaged with drill bit 100.

Referring to FIGS. 15 and 16, the operation of the adjustable depth stop 300 will now be described. In its initial state, the biasing spring 308 of the adjustable depth stop assembly 300 biases the shuttle sleeve 302 away from the locking/removal sleeves. Owing to the interaction of the corresponding tapered surfaces 344, 334, 374, 376 of the locking/removal sleeves and the sliding shuttle 310, this biasing causes the shuttle sleeve 302 (and so the sliding shuttle 310) to reside adjacent the distal end of the locking sleeve 304, thus causing the sliding shuttle 310 to laterally translate within the shuttle slot 324 such that lock ridge 368 of the sliding shuttle 310 engages one of the grooves 112 in the drill bit. The adjustable depth stop assembly 300 is thus locked to the drill bit 112.

To release the adjustable depth stop 300 from drill bit 100 the user may apply a force in the distal direction to the removal sleeve 306 while simultaneously applying a proximal force to the shuttle sleeve 302. When the user-applied force overcomes spring force the locking and removal sleeves 304 may move distally along the shuttle sleeve 302, which in turn translates sliding shuttle 310 laterally within shuttle slot 324, this time in the direction tending to separate the lock ridge 368 from the drill bit locking groove 112. The drill bit 100 may now slide freely within shuttle sleeve 302.

To select a desired drilling depth, the user may simply press the locking/removal sleeves while pulling back on the sliding shuttle, thus releasing stop assembly 300 from the drill bit 100 in the manner described above. The adjustable stop assembly 300 may then be moved along the drill bit 100 until the contact surface 322 of shuttle sleeve 302 lies adjacent the measured depth marking 110 corresponding to the desired drilling depth. The removal/locking sleeves may then be released, whereupon the spring may cause the sliding shuttle to engage the groove 112 in the drill bit 100 associated with the selected drilling depth.

Once the desired drilling depth has been selected, the distal end 220 of the distal housing 202 may be engaged with a targeted bone screw hole 32 of a bone plate 30, thus setting the appropriate drilling trajectory. Thereafter, a drilling device (either manual or powered) may be attached to the drill bit 100 proximal end 102 coupling. When drilling is begun, the user may simply apply a downward (distal) force to the drill bit 100 to overcome the force of spring 206, thus causing the drill distal end 104 to emerge from the distal housing 202 to engage the bone. While drilling is being performed, the adjustable depth stop assembly 300 may remain axially fixed with respect to the drill bit 100, and thus it may distally with the drill bit 100 as the drill tunnels into the bone. Since the housing 200 is axially fixed to the bone plate 30, maximum selected drilling depth is achieved when contact is made between the respective stop surfaces 258, 322 of the proximate housing 204 and the adjustable depth stop assembly 300. In relation to the above method of use, it is noted that the drilling depth may be adjusted after the housing 200 has been engaged with the bone plate 30.

It will be appreciated by one of ordinary skill in the art that the components of the invention may be constructed from a medical grade stainless steel that is tolerant of sterilization procedures and safe for use within the body. However, the device of the present invention may also be constructed from any suitable material that provides appropriate support for drilling bone holes. In one embodiment, the device may be constructed from a polymer based material such that the device is disposable following use. By way of example, but not limitation, suitable polymers may include ultra-high molecular weight polyethylene or the like.

Accordingly, it should be understood that the embodiments disclosed herein are merely illustrative of the principles of the invention. Various other modifications may be made by those skilled in the art which will embody the principles of the invention and fall within the spirit and the scope thereof.

What is claimed is:

1. A tool comprising:
   a drill bit having a proximal bit end, a distal bit end, the distal end configured to cut bone;
   a housing having a first end, a second end and a first bore configured to slidably receive the drill bit, the second end being adapted for association with a bone portion; and
   an adjustable depth stop assembly, having a proximal end, a distal end and a second bore configured to slidably receive the drill bit, comprising a portion configured to selectively lock the drill bit to the second bore, an adjustment sleeve configured to slidably engage the drill bit, and a shuttle member adapted to be slidable with respect to the adjustment sleeve between a first position in which the adjustable depth stop is axially locked to the drill bit and a second position in which the adjustable depth stop is axially movable with respect to the drill bit,
   wherein when the drill bit is locked to the adjustable depth stop assembly the first end of the housing is located a first axial distance from the distal end of the adjustable depth stop assembly, the first axial distance proportional to a maximum drilling depth into the bone portion.

2. The tool of claim 1, the second end of the housing further configured to engage the bone portion.

3. The tool of claim 1, the second end of the housing further configured to engage a bone fixation element.

4. The tool of claim 3, wherein the bone fixation element comprises a bone plate or a pedicle screw clamping element.

5. The tool of claim 3, wherein the bone fixation element comprises a bone plate and the second end of the housing is configured to engage a fastener hole of the plate.

6. The tool of claim 5, the second end of the housing further comprising threads configured to engage corresponding threads of the fastener hole.

7. The tool of claim 1, the second end of the housing further configured to engage a screw hole of a bone plate to fix the trajectory of the drill bit with respect to the bone plate and the bone portion.

8. The tool of claim 1, wherein the drill bit is axially positionable with respect to the housing, the drill bit further having an extended position in which the distal bit end of the drill bit extends distally beyond the second end of the housing.

9. The tool of claim 8, the drill bit further having a retracted position in which the distal bit end of the drill bit does not extend distally beyond the second end of the housing.

10. The tool of claim 9, the housing further comprising a spring having a first surface associated with the housing and a second surface associated with the drill bit, the spring operable to bias the drill in the retracted position.

11. The tool of claim 8, the drill bit further comprising an axial engagement portion configured to engage a corresponding axial engagement portion of the housing to prevent the distal bit end of the drill bit from moving axially past the first end of the housing.

12. The tool of claim 11, wherein the axial engagement portions of the drill bit and housing comprise a pin and a shoulder, respectively.

13. The tool of claim 1, the housing further comprising a proximal housing portion and a distal housing portion, the proximal housing portion comprising a spring operable to bias the drill in the retracted position, the distal housing portion comprising threads for engaging a bone screw hole of the a bone plate.

14. The tool of claim 13, the proximal end of the distal housing portion further comprising protrusion and recess elements configured to engage a respective recess and protrusion elements on the distal end of the proximal housing portion to rotationally fix the two housing portions.

15. The tool of claim 13, the housing further comprising a retainer for removably coupling the proximal and distal housing portions, wherein the housing portions may be disassembled to facilitate cleaning and/or sterilization of the tool.

16. The tool of claim 13, the proximal housing portion further comprising a proximal end having an increased diameter to allow gripping by a user.

17. The tool of claim 13, the proximal housing portion further having a proximal stop surface configured to engage the adjustable depth stop assembly.

18. The tool of claim 1, wherein moving the shuttle between first and second positions comprises moving the shuttle along an axis substantially perpendicular to the longitudinal axis of the drill bit.

19. The tool of claim 1, wherein moving the shuttle between first and second positions comprises moving the shuttle along an axis substantially non-parallel to the longitudinal axis of the drill bit.

20. The tool of claim 1, the shuttle further comprising a drill bit engaging surface, the drill bit further comprising a shuttle engaging surface.

21. The tool of claim 20, wherein one of the drill bit engaging surface and shuttle engaging surface comprises a projection and the other comprises a recess.

22. The tool of claim 1, the adjustable depth stop assembly further comprising a locking sleeve associated with the adjustment sleeve, the locking sleeve co-operable with the shuttle to move the shuttle between the first and second positions.

23. The tool of claim 22, the locking sleeve and shuttle further comprising corresponding tapered sliding surfaces each of which forms an oblique angle with respect to the longitudinal axis of the drill bit, wherein axial movement of the locking sleeve moves the shuttle between the first and second positions.

24. The tool of claim 20, wherein the shuttle is axially fixed to the adjustment sleeve, the locking sleeve is axially translatable along the adjustment sleeve, and wherein moving the locking sleeve along the adjustment sleeve in a first direction causes the shuttle to move toward the first position.

25. The tool of claim 24, wherein moving the locking sleeve along the adjustment sleeve in a second direction causes the shuttle to move toward the second position.

26. The tool of claim 1, the adjustable depth stop assembly further comprising a spring associated with the adjustment sleeve to bias the shuttle in the first position.

27. The tool of claim 1, the adjustment sleeve having a distal stop surface configured to engage a proximal stop surface of the housing.

28. A tool comprising:
a drill bit having a proximal bit end, a distal bit end and a longitudinal axis, the proximal bit end configured to connect to a driving attachment and the distal bit end having a cutting surface for cutting bone, the drill bit further having an extended position corresponding to a first drilling depth into bone;
a housing comprising a first end, a second end and a first longitudinal bore, the drill bit axially positionable within the first longitudinal bore, the first end further having a stop surface, the second end being adapted for association with a bone portion; and
an adjustable depth stop assembly, having a proximal end, a distal end and a second longitudinal bore, wherein the drill bit selectively axially lockable within the second longitudinal bore and the distal end comprises a stop surface configured to engage the housing stop surface, comprising an adjustment sleeve configured to slidably engage the drill bit, and a shuttle member adapted to be slidable with respect to the adjustment sleeve between a first position in which the adjustable depth stop assembly is axially locked to the drill bit and a second position in which the adjustable depth stop assembly is axially movable with respect to the drill bit,
wherein the adjustable depth stop assembly further has an unlocked and a locked configuration,
wherein the drill bit is axially translatable within the adjustable depth stop assembly when the adjustable depth stop assembly is in the unlocked position, and the drill bit axially fixed with respect to the adjustable depth stop assembly when the adjustable depth stop assembly is in the locked configuration, and
wherein adjusting the distance between the respective stop surfaces of the housing and the adjustable depth stop assembly adjusts the first drilling depth into the bone portion.

29. The tool of claim 28, the second end of the housing further configured to engage the bone portion.

30. The tool of claim 28, the second end of the housing further configured to engage a bone engaging element.

31. The tool of claim 30, wherein the bone engaging element comprises a bone plate or a pedicle screw clamping element.

32. The tool of claim 31, wherein the bone engaging element is a bone plate and the second end of the housing is configured to engage a fastener hole of the plate.

33. The tool of claim 32, the second end of the housing comprising threads configured to engage corresponding threads of the fastener hole.

34. The tool of claim 28, the second end of the housing further configured to engage a fastener hole of a bone plate, the second end comprising threads configured to engage corresponding threads of the hole in the plate.

35. The tool of claim 28, the second end of the housing further configured to engage a fastener hole of a bone plate to fix the trajectory of the drill bit with respect to the bone plate.

36. The tool of claim 28, the drill bit further having a retracted position in which the distal bit end of the drill bit does not extend distally beyond the distal second end of the housing.

37. The tool of claim 28, the housing further comprising a spring having a first surface associated with the housing and a second surface associated with the drill bit, the spring operable to bias the drill in the retracted position.

38. The tool of claim 28, the drill bit further comprising an axial engagement portion configured to engage a corresponding axial engagement portion of the housing to prevent the distal end of the drill bit from moving axially past the proximal end of the housing.

39. The tool of claim 38, wherein the axial engagement portions of the drill bit and housing comprise a pin and a shoulder, respectively.

40. The tool of claim 28, the housing further comprising a proximal housing portion and a distal housing portion, the proximal housing portion comprising a spring operable to bias the drill in the retracted position, the distal housing portion comprising threads for engaging a bone screw hole of the bone plate.

41. The tool of claim 40, the proximal end of the distal housing portion further comprising protrusion and recess elements configured to engage a respective recess and protrusion elements on the distal end of the proximal housing portion to rotationally fix the two housings.

42. The tool of claim 40, the housing further comprising a retainer for removably coupling the proximal and distal housing portions, wherein the proximal and distal housing portions can be decoupled to facilitate cleaning and/or sterilization of the tool.

43. The tool of claim 40, the proximal housing portion further comprising a proximal end having an increased diameter to allow gripping by a user.

44. The tool of claim 40, the proximal housing portion further having a proximal stop surface configured to engage the adjustable depth stop assembly.

45. The tool of claim 28, wherein moving the shuttle between first and second positions comprises moving the shuttle along an axis substantially perpendicular to the longitudinal axis of the drill bit.

46. The tool of claim 28, wherein moving the shuttle between first and second positions comprises moving the shuttle along an axis substantially non-parallel to the longitudinal axis of the drill bit.

47. The tool of claim 28, the shuttle further comprising a drill bit engaging surface, the drill bit further comprising a shuttle engaging surface.

48. The tool of claim 47, wherein one of the drill bit engaging surface and shuttle engaging surface comprises a projection and the other comprises a recess.

49. The tool of claim 26, the adjustable depth stop assembly further comprising a locking sleeve associated with the adjustment sleeve, the locking sleeve co-operable with the shuttle to move the shuttle between the first and second positions.

50. The tool of claim 49, the locking sleeve and shuttle further comprising corresponding tapered sliding surfaces each of which forms an oblique angle with respect to the longitudinal axis of the drill bit, wherein axial movement of the locking sleeve moves the shuttle between the first and second positions.

51. The tool of claim 49, wherein the shuttle is axially fixed to the adjustment sleeve, the locking sleeve is axially translatable along the adjustment sleeve, and wherein moving the locking sleeve along the adjustment sleeve in a first direction causes the shuttle to move toward the first position.

52. The tool of claim 49 wherein moving the locking sleeve along the adjustment sleeve in a second direction causes the shuttle to move toward the second position.

53. The tool of claim 28, the adjustable depth stop assembly further comprising a spring associated with the adjustment sleeve to bias the shuttle in the first position.

* * * * *